(12) United States Patent
Keller

(10) Patent No.: US 8,590,747 B2
(45) Date of Patent: Nov. 26, 2013

(54) MULTIPLE CARTRIDGE DISPENSER WITH ROTATING DRIVER

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 449 days.

(21) Appl. No.: 12/809,524

(22) PCT Filed: Jan. 7, 2009

(86) PCT No.: PCT/CH2009/000007
§ 371 (c)(1),
(2), (4) Date: Jun. 18, 2010

(87) PCT Pub. No.: WO2009/086650
PCT Pub. Date: Jul. 16, 2009

(65) Prior Publication Data
US 2010/0288790 A1    Nov. 18, 2010

(30) Foreign Application Priority Data
Jan. 11, 2008   (CH) .......................... 38/08

(51) Int. Cl.
*B67D 7/70*   (2010.01)
*B67D 1/00*   (2006.01)
*B67D 7/22*   (2010.01)
*B67D 7/78*   (2010.01)
*B67D 7/60*   (2010.01)
*G01F 11/00*  (2006.01)

(52) U.S. Cl.
USPC ............ 222/137; 222/39; 222/46; 222/145.6; 222/390

(58) Field of Classification Search
USPC ............ 222/135–137, 145.5, 145.6, 39, 390, 222/41–50
See application file for complete search history.

(56) References Cited

U.S. PATENT DOCUMENTS

| | | | |
|---|---|---|---|
| 3,082,914 A | * | 3/1963 | Gill ................................ 222/135 |
| 3,185,345 A | * | 5/1965 | Hunegs ........................... 222/45 |
| 3,952,920 A | | 4/1976 | Bergman |
| 4,046,288 A | * | 9/1977 | Bergman ....................... 222/135 |
| 4,240,566 A | * | 12/1980 | Bergman ....................... 222/135 |
| 4,429,724 A | * | 2/1984 | Dorros et al. ................... 141/27 |
| 4,552,155 A | * | 11/1985 | Etherington et al. .......... 600/579 |

(Continued)

FOREIGN PATENT DOCUMENTS

| | | |
|---|---|---|
| DE | 101 28 611 A1 | 12/2002 |
| DE | 20 2006 011 103 U1 | 1/2008 |

(Continued)

*Primary Examiner* — Paul R. Durand
*Assistant Examiner* — Matthew Lembo
(74) *Attorney, Agent, or Firm* — Foley & Lardner LLP

(57) ABSTRACT

A dispensing appliance for a double cartridge comprises a housing for receiving multiple components and a rotatable portion having a thread, the two parts cooperating in such a manner that by rotating the rotatable portion, a multiple plunger acting upon the pistons in the housing is continuously displaceable relative to the housing in the dispensing direction. To this end, the housing is configured to comprise at least two adjacent storage containers, and the thrust force of the rotatable portion is directly transmitted to a multiple plunger. The rotatable portion may have an internal thread and the double plunger a feed flange with a corresponding external thread, in order to actuate the latter in the axial direction upon rotation of the rotatable portion. This arrangement allows dispensing even highly viscous materials with little manual force under high pressure in a precisely metered manner.

13 Claims, 3 Drawing Sheets

(56) References Cited

U.S. PATENT DOCUMENTS

Figure 1:
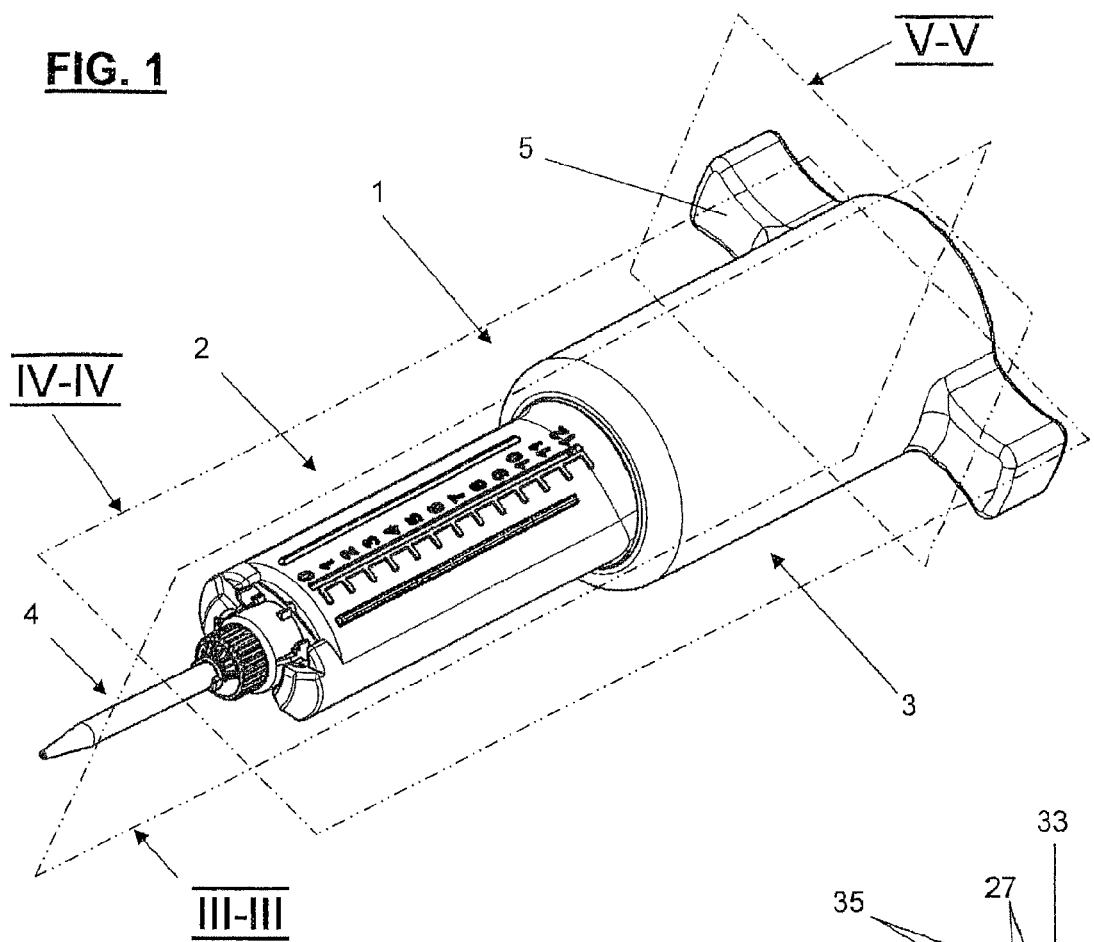

| | | | |
|---|---|---|---|
| 4,623,337 A | 11/1986 | Maurice | |
| 4,871,088 A * | 10/1989 | Cox | 222/47 |
| 5,033,650 A * | 7/1991 | Colin et al. | 222/137 |
| 5,143,259 A * | 9/1992 | Williams | 222/80 |
| 5,271,527 A * | 12/1993 | Haber et al. | 222/43 |
| 5,535,922 A | 7/1996 | Maziarz | |
| 6,022,163 A * | 2/2000 | Asfur | 401/175 |
| 6,176,396 B1 * | 1/2001 | Hamada et al. | 222/137 |
| 6,569,126 B1 * | 5/2003 | Poulsen et al. | 604/207 |
| 7,086,564 B1 * | 8/2006 | Corrigan | 222/39 |
| 7,303,348 B2 * | 12/2007 | Phipps et al. | 401/175 |
| 2002/0166878 A1 | 11/2002 | Mizutani et al. | |
| 2003/0057236 A1 * | 3/2003 | Delage | 222/390 |
| 2003/0089743 A1 | 5/2003 | Py et al. | |
| 2004/0216591 A1 | 11/2004 | Assadi et al. | |
| 2005/0072811 A1 * | 4/2005 | Heiberger | 222/389 |
| 2007/0072146 A1 | 3/2007 | Pierson | |
| 2007/0164048 A1 * | 7/2007 | Lou | 222/137 |

FOREIGN PATENT DOCUMENTS

| | | |
|---|---|---|
| EP | 0 621 083 B1 | 7/1996 |
| FR | 1.179.121 | 5/1959 |
| GB | 2 434 136 B | 7/2007 |
| WO | WO 2008/009143 A1 | 1/2008 |
| WO | WO 2008/009440 A1 | 1/2008 |

\* cited by examiner

MULTIPLE CARTRIDGE DISPENSER WITH ROTATING DRIVER

The present invention relates to a dispensing appliance for a multiple cartridge, comprising a housing for receiving the cartridge and a rotatable portion having a thread.

A dispensing appliance of this kind is known from DE-20 2006 011 103 U1, where the rotatable portion that is actuated by a knurled wheel is in the form of a threaded spindle acting upon the internal thread of a U-shaped plunger carrier and actuating the latter upon rotation. In the case of highly viscous materials, a relatively high force has to be produced by the knurled wheel so that a precise metering is difficult.

A number of further dispensing appliances are known where a part of the housing is rotatable with respect to the other part in order to dispense pharmaceutical products, e.g. from US-A1-2003/0089743; US-A1-2002/0166878, DE-A1-101 28 611, and U.S. Pat. No. 4,623,337. All these appliances are designed for single component cartridges, which are less problematic than multicomponent cartridges by nature.

Another group of dispensing appliances actuated by a rotary motion and having two adjacent storage containers are disclosed in U.S. Pat. No. 3,952,920 and EP-A1-0 621 083 where a central threaded rod acts upon the dispensing plungers.

Furthermore, a variety of manually operated dispensing appliances for a double cartridge or syringe for dispensing two-component materials are available on the market, e.g. according to U.S. Pat. No. 5,535,922, which are designed in the manner of a gun and where the force transmitted to a lever actuates the double plunger via a transmission mechanism. During the regrasp movement of the transmission mechanism, the double plunger is relieved and a total pressure relief of the cartridge is caused, thereby interrupting the material flow. An accurately metered operation as it is advantageous particularly in the application of bone cements is thus impossible. Furthermore, in the case of highly viscous materials, limits are imposed on such appliances by the fact that either a high multiplication ratio is required and thus a complicated mechanism, or high forces have to be applied, which is disadvantageous for difficult surgical applications.

Finally, WO 2008/009143 discloses a dispensing appliance for multiple components where an external rotatable portion is rotatable with respect to the inner housing portion comprising the cartridge and longitudinally displaceable in order to actuate a double plunger. Therewith, the total length of the appliance changes, which is disadvantageous for difficult surgical applications.

On the background of this prior art, it is the object of the present invention to provide a screw feed dispensing appliance that is suitable for multiple cartridges or multiple syringes having at least two adjacent storage containers, whose construction is simple, and that allows even highly viscous materials to be continuously and accurately dispensed with a relatively low manual force expenditure while the total length of the appliance does not change during dispensing.

This is accomplished by a dispensing appliance as described in the embodiments of the present application.

The invention will be explained in more detail hereinafter with reference to drawings of exemplary embodiments.

Figure 2:
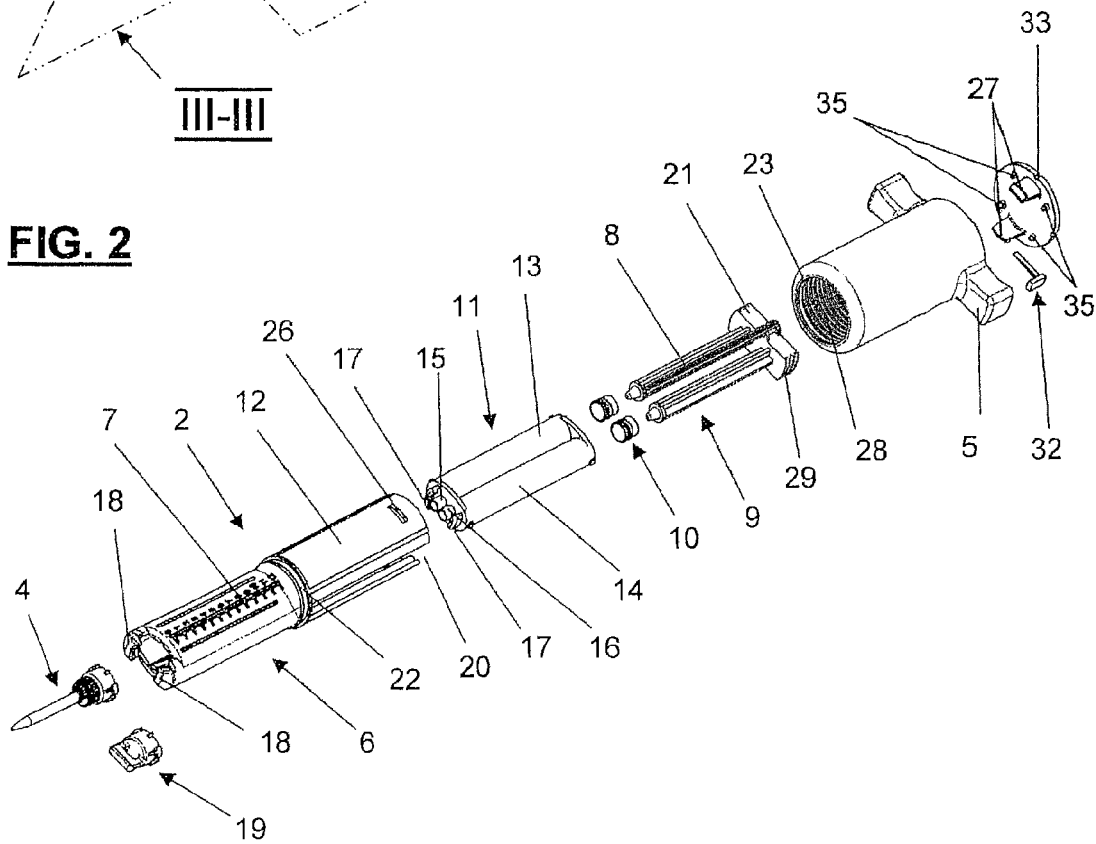
Figure 3:
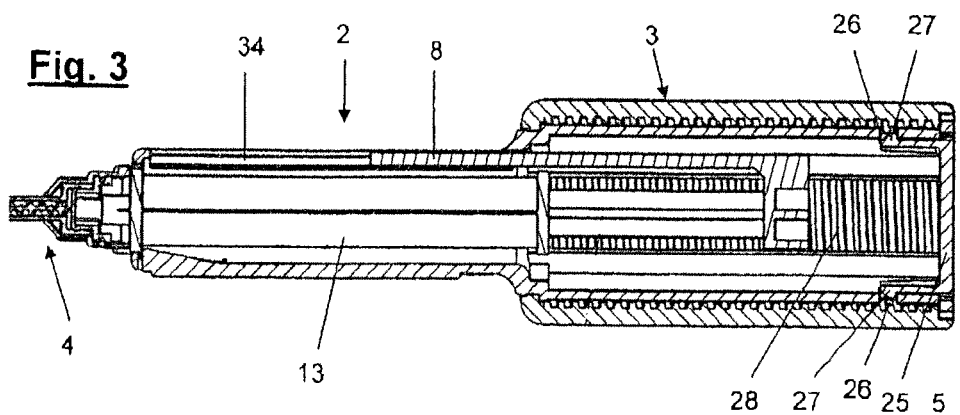
Figure 4:
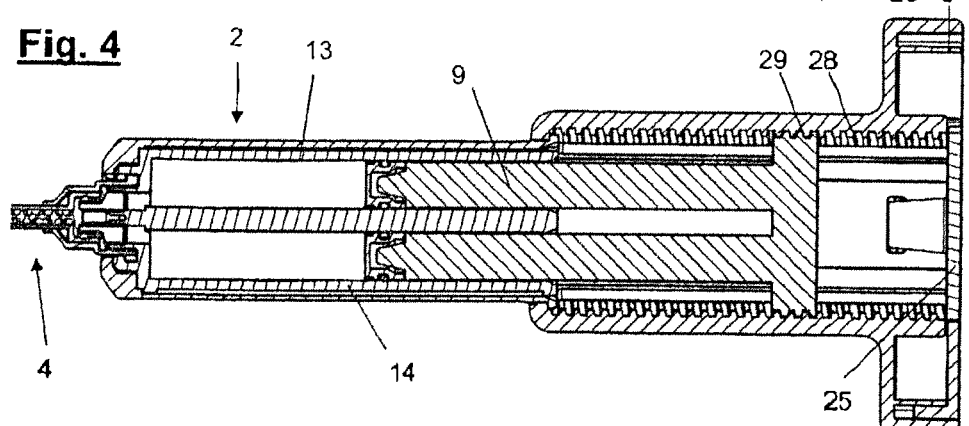
Figure 5:
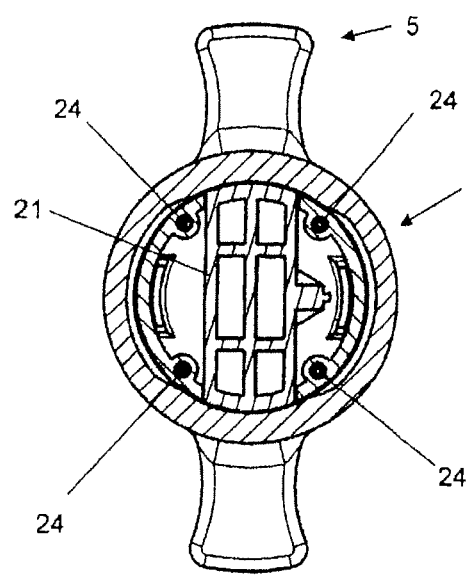
Figure 6:
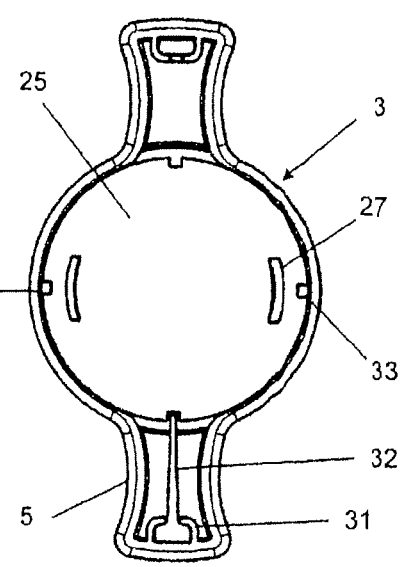
Figure 7:
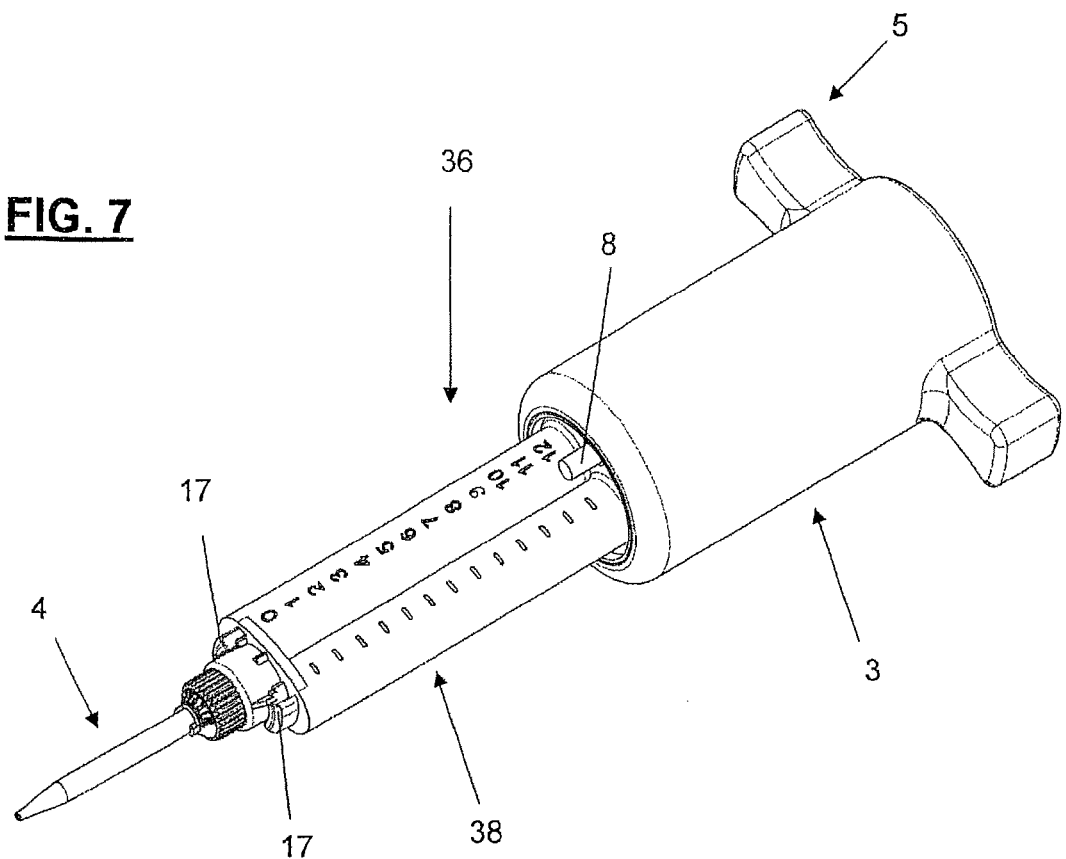
Figure 8:
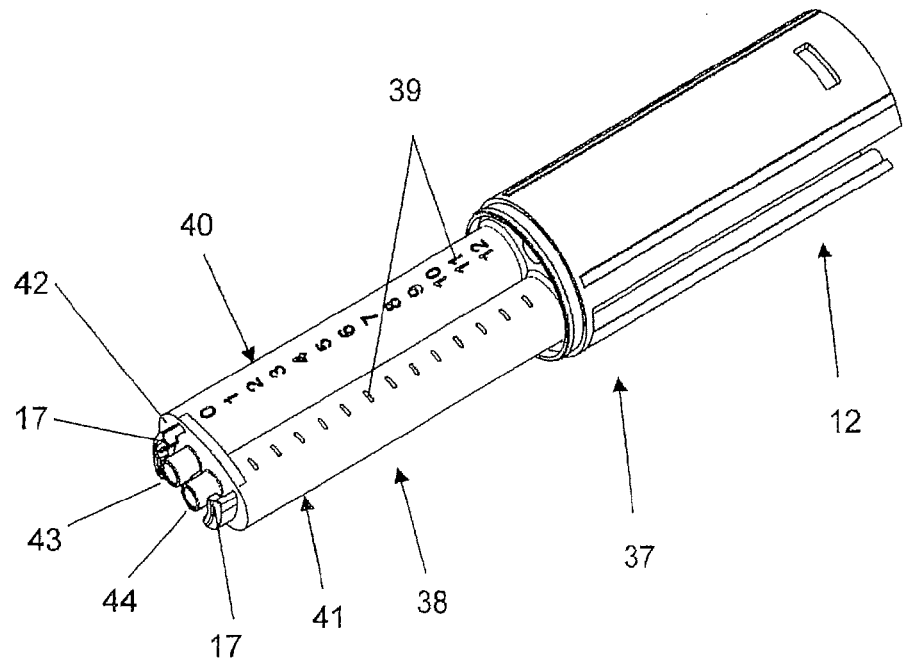

FIG. 1 shows a first exemplary embodiment of a dispensing appliance according to the invention in a perspective view, FIG. 2 shows the dispensing appliance of FIG. 1 in an exploded view, FIG. 3 shows a longitudinal section according to plane III-III in FIG. 1, FIG. 4 shows a longitudinal section according to plane IV-IV in FIG. 1, FIG. 5 shows a cross-section according to plane V-V in FIG. 1, FIG. 6 shows a view of the rear end of the device of FIG. 1, FIG. 7 shows a second exemplary embodiment of a dispensing appliance according to the invention in a perspective view, and FIG. 8 shows the housing of the dispensing appliance of FIG. 7.

As appears in the drawings, the principle of the dispensing appliance according to the invention is based on the relative rotation of two parts with respect to one another, whereby a continuous and accurately metered feed can be achieved. Hereinafter, the term "double cartridge" in the exemplary embodiment stands for a multiple cartridge or syringe. In this regard, it is apparent to one skilled in the art that in the case of more than two storage containers, a corresponding number of pistons and plungers will have to be provided.

FIG. 1 shows a first exemplary embodiment of an assembled dispensing appliance 1 according to the invention having a housing 2, a rotatable portion 3 with wing members 5 and a mixer 4 that is known per se. Section 6 on the outlet side of the housing is provided with a graduation 7 that cooperates with a filling level rod 8 on double plunger 9. The double plungers act upon pistons 10 of double cartridge 11 that is arranged in guiding portion 12 of housing 2.

Double cartridge 11 has two adjacent storage cylinders 13 and 14 having each the same diameter or different diameters or volumes, respectively.

The double cartridge further comprises the two outlets 15 and 16 as well as bayonet members 17, which form bayonet slots. As appears in FIGS. 1 and 2, the bayonet members 17 are radially and axially supported by correspondingly shaped bayonet slot reinforcement members 18 at the outlet side distal end of housing 2. The bayonet slot reinforcement members 18 are hook shaped, with an inwardly extending flange at their distal end, and are arranged in a radially surrounding configuration relative to the bayonet members 17. Each bayonet member 17 axially abuts to the inwardly extending flange of a corresponding bayonet slot reinforcement member 18.

Guiding portion 12 has two opposed guide slots 20 in which feed flange 21 of double plunger 9 slides, see in particular FIG. 5. At the transition of guiding portion 12 and housing section 6 on the outlet side thereof, a step 22 is arranged which cooperates with a stop collar 23 at the outlet side end of rotatable portion 3 in order to provide a bearing for the rotatable portion.

In the present exemplary embodiment, the end face on the inlet side of guiding portion 12 has four centering bores 24 for receiving four corresponding centering pins 35 of closure plate 25, see FIGS. 5 and 2. Also in the end section of guiding portion 12, two snap apertures 26 are internally provided which cooperate with two snap noses 27 on closure plate 25 in order to fasten the latter to the inlet side end of the guiding portion and thus to connect the two guiding members and simultaneously close the appliance on the rear side.

Rotatable portion 3 has an internal thread 28 that cooperates with external thread 29 provided on feed flange 21 of double plunger 9 in order to move the latter toward the outlet or back upon rotation of the rotatable portion, see in particular FIGS. 3 and 4.

In FIG. 3 it appears that filling level rod 8 is guided in a guide groove 34 arranged in the interior of housing section 6.

During dispensing by means of the rotatable portion, it is very advantageous for a surgeon to be able not only to read the filling level but also to count the dispensed volume units by means of acoustic signals. For this purpose, wing members 5 comprise a retaining arrangement 31 in which a sound bar 32 is received whose end engages in one of e.g. four symmetrically arranged notches 33 in closure plate 25 and produces a click during the rotation.

The figures, particularly also FIGS. 3 and 4, illustrate the assembly and the operation of the dispensing appliance. First, the cartridge provided with the piston and the closing cap is completely inserted into housing 2 and subsequently, the double plunger is placed in guiding portion 12, after which the rotatable portion is pushed onto the housing from the outlet side and the internal thread is fully engaged in the external thread of the feed flange of double plunger 9, whereupon the closure plate is put on and snapped in.

For dispensing, the closing cap is removed from the double cartridge and a mixer is attached, after which the dispensing appliance is ready for use. For dispensing, the rotatable portion is rotated with respect to the housing, a sound being produced at each quarter turn and the dispensed quantity being indicated by the position of the filling level rod.

FIG. 7 shows a second exemplary embodiment of an assembled dispensing appliance 36 according to the invention having a housing 37, rotatable portion 3 with wing members 5, and mixer 4. Section 38 on the outlet side of the housing is provided with a graduation 39 that cooperates with a filling level rod 8 on double plunger 9.

In contrast to the first exemplary embodiment, section 38 on the outlet side is in the form of a double container 40, 41 whereas bayonet slots 17 are arranged on outlet flange 42 around outlets 43, 44 and the filled double container is sealed by means of pistons. Guiding portion 12 is the same as in the first exemplary embodiment and has the same guide slots 20. The remaining parts are the same as in the first exemplary embodiment too.

The second exemplary embodiment allows an inexpensive manufacture of a dispensing appliance comprising containers without a loss in accuracy and ease of handling.

The invention claimed is:

1. A dispensing appliance for multiple components, comprising:
    a housing that is configured to receive at least two adjacent storage containers for receiving the multiple components;
    a multiple plunger configured to act upon pistons in the housing, the multiple plunger including a feed flange, the feed flange having an external thread;
    a rotatable portion having an internal thread that is operatively connected to the external thread on the feed flange in order to displace the multiple plunger relative to the housing in an axial dispensing direction upon rotation of the rotatable portion, a thrust force being directly transmitted from the rotatable portion to the multiple plunger without altering a total length of the dispensing appliance; and
    a multiple cartridge or syringe that forms the at least two adjacent storage containers, the multiple cartridge or syringe being received in the housing, the housing and the multiple cartridge or syringe being separate parts,
    wherein the multiple cartridge or syringe comprises, at an outlet end thereof, bayonet members forming bayonet slots, and wherein the housing comprises, at an outlet end thereof, bayonet slot reinforcement members, the bayonet slot reinforcement members supporting the bayonet members.

2. The dispensing appliance according to claim 1, wherein an end of the rotatable portion on an outlet side thereof is supported rotatably on the housing.

3. The dispensing appliance according to claim 2, wherein the feed flange is guided non-rotatably in two guide slots provided in a guiding portion of the housing.

4. The dispensing appliance according to claim 1, wherein a distal section of the housing is provided with a graduation that cooperates with a filling level rod arranged on the multiple plunger in order to indicate a dispensed volume.

5. The dispensing appliance according to claim 4, wherein the filling level rod is guided in a guide groove arranged in the interior of the distal section of the housing.

6. The dispensing appliance according to claim 1, further comprising means that audibly indicate a rotation of the rotatable portion about a certain rotation angle.

7. The dispensing appliance according to claim 6, wherein the audible means includes a sound bar that is fastened to the rotatable portion and engages in notches in a closure plate in order to produce a clicking sound.

8. The dispensing appliance according to claim 1, wherein the housing is configured to receive the multiple cartridge or syringe from a proximal end that is opposite to the outlet end of the housing.

9. The dispensing appliance according to claim 1, wherein the bayonet slot reinforcement members radially support the bayonet members.

10. The dispensing appliance according to claim 1, wherein the bayonet slot reinforcement members axially support the bayonet members.

11. The dispensing appliance according to claim 1, wherein the bayonet slot reinforcement members are arranged in a radially surrounding configuration relative to the bayonet members.

12. The dispensing appliance according to claim 1, wherein the bayonet members axially abut to the bayonet slot reinforcement members.

13. The dispensing appliance according to claim 1, wherein the bayonet reinforcement members are hook-shaped, each bayonet reinforcement member having an inwardly extending flange, and
    wherein each bayonet member axially abuts to the inwardly extending flange of a corresponding bayonet slot reinforcement member.

* * * * *